(12) United States Patent
Byun et al.

(10) Patent No.: US 6,342,034 B1
(45) Date of Patent: Jan. 29, 2002

(54) PROCESS FOR THE PREPARATION OF L-CARNITINE

(75) Inventors: Il Suk Byun; Kyung Il Kim; Chan Ah Bong, all of Taejeon (KR)

(73) Assignee: Samsung Fine Chemicals Co., Ltd. (KR)

(*) Notice: Subject to any disclaimer, the term of this patent is extended or adjusted under 35 U.S.C. 154(b) by 0 days.

(21) Appl. No.: 09/463,443

(22) PCT Filed: Jun. 17, 1998

(86) PCT No.: PCT/KR98/00165

§ 371 Date: Jan. 27, 2000

§ 102(e) Date: Jan. 27, 2000

(87) PCT Pub. No.: WO99/05092

PCT Pub. Date: Feb. 4, 1999

(30) Foreign Application Priority Data

Jul. 28, 1997 (KR) .............................. 97-35473
Nov. 3, 1997 (KR) .............................. 97-57813

(51) Int. Cl.$^7$ ............................... C07C 229/00
(52) U.S. Cl. .................................... 567/567
(58) Field of Search ........................ 562/567

(56) References Cited

U.S. PATENT DOCUMENTS

| | | | |
|---|---|---|---|
| 4,254,053 A | 3/1981 | deWitt et al. |
| 4,371,618 A | 2/1983 | Cavazza |
| 4,413,142 A | 11/1983 | Fiorini et al. |
| 4,610,828 A | 9/1986 | Kikuchi |
| 4,650,759 A | 3/1987 | Yokozeki et al. |
| 4,933,490 A | 6/1990 | Iannella |
| 5,187,093 A | 2/1993 | Kulla et al. |
| 5,248,601 A | 9/1993 | Francalanci et al. |
| 5,292,939 A | 3/1994 | Hollingsworth |
| 5,319,110 A | 6/1994 | Hollingsworth |
| 5,374,773 A | 12/1994 | Hollingsworth |
| 5,473,104 A | 12/1995 | McCarthy |

FOREIGN PATENT DOCUMENTS

| | | |
|---|---|---|
| EP | 60595 | 9/1982 |
| EP | 0 157 315 A2 | 10/1985 |
| EP | 0 237 983 A2 | 9/1987 |
| EP | 0 457 735 A1 | 11/1991 |
| JP | 59-231048 | 12/1984 |
| JP | 1-131143 | 5/1989 |

OTHER PUBLICATIONS

Rossiter, B.E. et al., "Asymmetric Epoxidation of Homoallylic Alcohols. Synthesis of (−)-γ-Amino-β(R)-Hydroxybutyric Acid (GABOB)", American Chemical Society: J. Org. Chem., vol. 49 No. 20, p. 3707–3711, (1984).

Mohr, P. et al., "17.3-Hydroxyglutarate and β, γ-Epoxy Esters as Substrates for Pig Liver Esterase (PLE) and α-Chymotrypsin", Helvetica Chimica Acta, vol. 70, p. 142–152, (1987).

Fritz, I.B. et al., "Carnitine Acetyltransferase: II. Inhibition by Carnitine Analogues and by Sulfhydryl Reagents", The Journal of Biological Chemistry, vol. 240 No. 5, pp. 2188–2192, (1965).

Bellamy, F.D. et al., "A New, Short and Efficient Synthesis of Both Enantiomers of Carnitine", Tetrahedron Letters, vol. 31 No. 50, p. 7323–7326, (1990).

*Primary Examiner*—Gary Geist
*Assistant Examiner*—Leigh C. Maier
(74) *Attorney, Agent, or Firm*—Finnegan, Henderson, Farabow, Garrett & Dunner, L.L.P.

(57) ABSTRACT

A process for the preparation of L-carnitine using (S)-3-activated hydroxybutyrolactone as a raw material, which is subject to a ring-opening reaction, expoxydation where the chiral center is inversely converted, and nucleophilic substitution of trimethylamine.

19 Claims, No Drawings

PROCESS FOR THE PREPARATION OF L-CARNITINE

This application is the National Stage filing under 35 USC 371 of PCT/KR98/00165, filed Jun. 17, 1998.

BACKGROUND OF THE INVENTION

1. Field of the Invention

The present invention relates to the process for the preparation of L-carnitine expressed by the following formula 1, which is useful in industrial mass production due to the fact that each reaction in the aqueous solution phase is continuously carried out in a reactor without separate purification process. More particularly, this invention relates to such process, wherein (S)-3-activated hydroxybutyrolactone is utilized as a raw material so as to undergo the following chemical reactions under the specific conditions: a ring-opening reaction, epoxydation where the chiral center is inversely converted, and nucleophilic substitution of trimethylarmine.

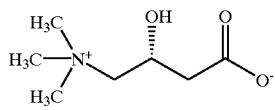

(1)

2. Description of the Prior Art

Carnitine occurs as two enantiomers, L- and D-isomers, in terms of its stereostructural characteristics although naturally-occurring carnitine in vivo is almost exclusively the L-isomer.

L-carnitine, also known as vitamin $B_T$, is present in the body tissues of animals including human and serves several vital roles. Thus, researchers have systematically focused on the physiological roles of L-carnitine. In particular, L-carnitine in vivo reacts with fatty acids with long chains which cannot pass through the mitochondria membrane. After such reaction, said fatty acids are converted into the membrane-permeable derivatives. In this pathway, L-carnitine plays a vital role in degrading the fatty acids in mitochondria via oxidation for energy source.

Meanwhile, the D,L-carnitine racemate has been used as a pharmaceutical drug or food additive in the past, but D-carnitine has been reported to have a competitive interference effect against the physiological roles of L-carnitine in vivo [Fritz, I. B., Schultz, S. K., J. Biol. Chem. (1965) 240 2188; Roe, C. R., Bohan, T. P., Lancet (1982) 1411]. Recently, there has been a trend of selectively using the optically pure L-carnitine instead of the D,L-carnitine racemate. Therefore, many of the references or patents include active research on the topic of obtaining an optically pure L-carnitine.

The conventional methods relating to the preparation of the optically pure L-carnitine are as follows:

First, according to the chemical optical resolution method, D,L-carnitine or the racemate of its derivatives is reacted with an optically pure chiral optical resolution agent to yield diastereoisomers. Then, the target diastereoisomer is obtained by resolution using the difference of solubility in an appropriate solvent. The above compound is again hydrolyzed so as to yield the target L-carnitine. The commonly used optical resolution agent includes D-camphoric acid [U.S. Pat. No. 4,254,053 (1981)], L-tartaric acid [European Patent 157,315 (1985)], dibenzoyl-D-tartaric acid [U.S. Pat. No. 4,933,490 (1990)], dibenzoyl-L-tartaric acid [U.S. Pat. No. 4,610,828 (1986)], D-mandelic acid [Japanese Unexamined Patent Publication Sho 59-231,048 (1984)], and N-acetyl-D-glutamic acid [Japanese Unexamined Patent Publication Hei 1-131,143 (1989)]. However, the aforementioned chemical optical resolution method has recognized disadvantages in that a) high-priced optical resolution agent would be inevitably used, b) the process of recovering such agent would be essential, c) the optical resolution is extremely difficult during the re-crystallization step for the formation of the diastereoisomer.

Second, there is a biological method for preparing L-carnitine using microorganisms or enzymes. L-carnitine is produced from butyrobetaine as a raw material by means of stereo-selective hydroxylation with pertinent enzymes [U.S. Pat. No. 4,371,618 (1983), U.S. Pat. No. 5,187,093 (1993)], or from crotonobetaine as a raw material by means of stereoselective hydration with appropriate enzymes [U.S. Pat. No. 4,650,759 (1987), U.S. Pat. No. 5,248,601 (1993), European Patent 457,735 (1991)]. However, these methods also have recognized disadvantages in that a) a longer reaction time of 2~3 days is required, and b) unlike the chemical reaction, the reaction concentration is extremely low as is the characteristic of the biological reactions.

Further, there is another biological method for preparing L-carnitine via the reaction between (R)-3,4-epoxybutyric acid and trimethylamine [Helvetica Chimica Acta, vol. 70, 142~152 (1987); European Patent 237,983 (1987)]. (R)-3,4-epoxybutyric acid as a main raw material undergoes a chemical reaction to yield a racemic 3,4-epoxybutyric acid ester. Based on the biological method, such ester undergoes optical resolution to yield (R)-3,4-epoxybutyric acid ester selectively, which is again hydrolyzed to produce the target compound. This method has proven to have an excellent stereo-selectivity although a careful modulation of reaction is required as is typical of the biological reaction with a prolonged reaction time of approximately 24 hours.

Third, there is the method of preparing L-carnitine by means of utilizing chiral material from the natural source. According to such method, D-mannitol is employed as a raw material. Then, via various reaction steps, L-carnitine is prepared [European Patent 60,595 (1982)]. However, this method also has recognized disadvantages in that a) the reaction steps are very complicated, and b) heavy metal compounds such as tetraacetyl lead must be employed. Further, the process of preparing L-carnitine from D-(R)-tartaric acid has been reported in the literature [Tetrahedron Letters, vol.31, 7323~7326 (1990)], but in such case, many complicated manufacturing steps are required.

Another method of preparing L-carnitine from (S)-3-activated hydroxybutyrolactone has been disclosed [U.S. Pat. No. 5,473,104 (1995)]. According to this method, (S)-3-methanesulfonyl hydroxybutyrolactone of 1.0 equivalent, and 25% trimethylarmine solution of 2.0 equivalent are mixed. Then, the mixture in a closed container is stirred at room temperature for 1 hour. In addition, the mixture is reacted at 100° C. for 16 hours to produce pure L-carnitine, but the yield is not mentioned. The above method has disclosed that as the assumed reaction routes, the following successive reactions may be implemented: A ring-opening reaction, epoxydation where the chiral center is inversely converted, and nucleophilic substitution by trimethylamine.

However, reproduction of the results therefrom could not be confirmed since L-carnitine was not obtainable based on the examples herein. To examine the method in a more accurate manner, the reaction solution was analyzed with nuclear magnetic resonance and a results showed very little amount of L-carnitine.

The optically pure 3-hydroxybutyrolactone has seldom been utilized as a chiral raw material in the past due to the difficulty in its preparation. But, recently, the very inexpensive and facile method of preparing (S)-3-hydroxybutyrolactone through oxidation and successive cyclization from inexpensive natural D-carbohydrates and hydrogen peroxide has been developed (U.S. Pat. Nos. 5,292,939, 5,319,110, 5,374,773). As a result, (S)-3-hydroxybutyrolactone is being utilized as a pivotal raw material in the preparation of various chiral compounds, and the extent of its use will be expanded.

SUMMARY OF THE INVENTION

As a result of the intensive studies to overcome the problems associated with the process of preparing L-carnitine, the invention herein has been devised based on the fact that the following reactions can be carried out with (S)-3-activated hydroxybutyrolactone as a raw material under the specific conditions: a ring-opening reaction, epoxydation where the chiral center is inversely converted, and nucleophilic substitution of trimethylamine. Where reaction conditions are duly designated under said invention, the purity and yield at each reaction step are relatively high to the point that separate purification process is not required with the result of achieving the one-pot reaction herein.

Therefore, the objective of this invention is to provide a process for preparing highly pure L-carnitine with a high yield using inexpensive compounds in the aqueous solution.

DETAILED DESCRIPTION OF THE INVENTION

The present invention relates to the process for preparing of L-carnitine of the following formula 1 from (S)-3-activated hydroxybutyrolactone, wherein (S)-3-activated hydroxybutyrolactone of the following formula 2 is subjected to a ring-opening reaction in the aqueous solvent;

based on the above reaction, 4hydroxy-3-activated hydroxybutyric acid of the following formula 3 is prepared therefrom;

4-hydroxy-3-activated hydroxybutyric acid of said formula 3 is subjected to an inverse conversion reaction at the chiral center in the presence of a base for the preparation of the salt of 3,4-epoxybutyric acid of the following formula 4; and both the salt of 3,4-epoxybutyric acid of said formula 4 and trimethylamine undergo nucleophilic substitution,

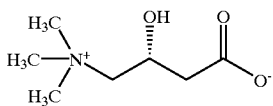

(1)

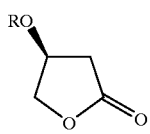

(2)

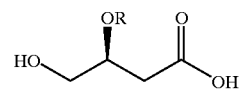

(3)

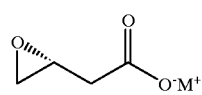

(4)

wherein R is an alkylsulfonyl, arylsulfonyl, acyl, or phosphoryl group.

The present invention is explained in more detail as set forth hereunder. Unlike the conventional method of preparing L-carnitine, this invention is a highly economical process, wherein the chiral center is inversely converted so that highly pure L-carnitine may be obtained with a high yield.

The following scheme 1 shows the process for the preparing L-carnitine according to this invention:

Scheme 1

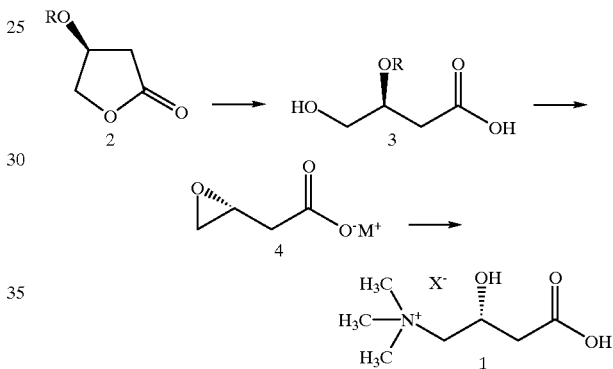

wherein R is introduced for the purpose of activating the hydroxy group and includes an alkylsulfonyl, arylsulfonyl, acyl group, or phosphoryl group. $M^+$ is determined by the base used herein.

(S)-3-activated hydroxybutyrolactone of formula 2 as the starting material of this invention is a compound, which is activated for the purposes of nucleophilic substitution of the hydroxy group in (S)-3-hydroxybutyrolactone.

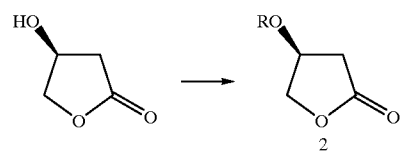

Various chemical methods designed to activate the hydroxy group have been disclosed including sulfonylation, acylation and phosphorylation. Among these methods, the sulfonylation is typically used. The sulfonylation agent includes an alkylsulfonic acid anhydride, alkylsulfonyl chloride or arylsulfonyl chloride. Hence, alkylsulfonyl refers to alkylsulfonyl or haloalkylsulfonyl of $C_{1\sim12}$, or more specifically includes methanesulfonyl, ethanesulfonyl, isopropanesulfonyl, chloromethanesulfonyl, trifluoromethanesulfonyl and chloroethanesulfonyl. Arylsulfonyl includes benzenesulfonyl, toluenesulfonyl, haloarylsulfonyl such as chlorobenzenesulfonyl or bromobenzenesulfonyl, naphthalenesulfonyl, alkoxyaryl, sulfonyl of $C_{1\sim4}$ such as methoxybenzenesulfonyl and nitroarylsulfonyl. The compound expressed by formula 2, prepared via said activation reaction, includes (S)-3-alkylsulfonylhydroxybutyrolactone, (S)-3-arylsulfonyl hydroxybutyrolactone, and so on. For this purpose, (S)-3-methanesulfonyl hydroxybutyrolactone is generally used.

The first reaction step is a ring-opening reaction of (S)-3-activated hydroxybutyrolactone expressed by formula 2. The ring-opening reaction of this invention is similar to the reaction in which the ester group is hydrolyzed. However, in view of the reaction mechanism, the general hydrolysis method cannot work due to the presence of the 3-activated hydroxy group which is easily detachable at the β-position of the carbonyl group of the compound of formula 2. In this regard, several commonly known hydrolysis methods have been implemented, but the ring-opening reaction did not occurred with respect to the compound of formula 2. Therefore, the target compound of formula 3 under this invention could be not be obtained. For example, the hydrolysis of the esters using water as a solvent in the presence of sodium hydroxide is known to be irreversible and quantitative. However, when the ring-opening reaction of 3-methanesulfonylhydroxybutyrolactone was attempted among the compounds of formula 2, the compounds without the sulfonylhydroxy group (—OR) were mainly obtained. In addition to sodium hydroxide, various types of bases (e.g., inorganic bases such as potassium hydroxide, or organic amines such as triethylamine and pyridine) have been used in order to carry out the ring-opening reaction. However, the compounds without the sulfonylhydroxy group (—OR) were obtained as main products instead of the target compound of this invention. In particular, based on the U.S. Pat. No. 5,473,104 (1995), (S)-3-methanesulfonyl hydroxybutyrolactone of 1 equivalent and 25% trimethylamine solution of 1~2 equivalent as a base were mixed. Then, the mixture was stirred and reacted at room temperature. However, the ring-opening reaction was not implemented, and within 10 minutes, it was confirmed by nuclear magnetic resonance analysis that furanone without the methanesulfonyl group was formed in 70~100% yield. Therefore, L-carnitine could not be formed under the above reaction conditions.

In an effort to examine the effect of (S)-3-activated hydroxy group (—OR) in the above ring-opening reaction, the reaction was carried out with 3-hydroxybutyrolactone with an inactivated hydroxy group under the same reaction conditions. As a result, the target compound of 3,4-hydroxybutyric acid could be quantitatively obtained without dehydration.

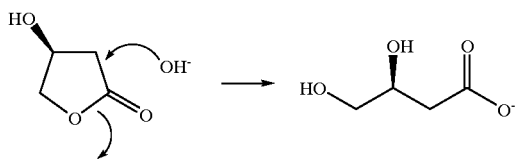

From the above test results, hydrogen at the α-position of (S)-3-activated hydroxybutyrolactone expressed by said formula 2 has higher acidity due to the influence of the carbonyl group. Consequently, the base initially attacks the hydrogen at the α-position prior to its attack on the carbonyl group to give the result of eliminating the sulfonylhydroxy group.

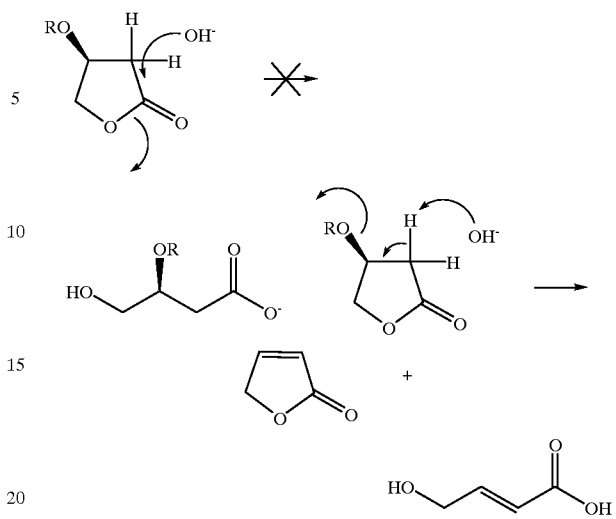

Based on the above results, the ring-opening reaction was attempted in the presence of acid catalyst under the assumption that the hydrogen at the α-position of the carbonyl group may be stabilized without removal in the acidic condition. The acid catalysts include inorganic acids such as sulfuric acid, hydrochloric acid and phosphoric acid, or organic acids such as methanesulfonic acid, toluenesulfonic acid and camphorsulfonic acid. Water is employed as a single solvent in the reaction, but in order to enhance the solubility of (S)-3-activated hydroxybutyrolactone as the starting material, an organic co-solvent with water may be utilized, such as alcohol of $C_{1\sim4}$, tetrahydrofuran, or acetonitrile. It is preferable that the mixing ratio between water and the organic solvent be approximately 95:5(v/v)~50:50 (v/v).

For example, among the compounds under formula 2,3-methanesulfonyl hydroxybutyrolactone was used in the presence of sulfuric acid catalyst of 0.1 equivalent in water as a solvent. Then, the reaction mixture was stirred at 50° C. for 3 hours. The results of nuclear magnetic resonance analysis of the reaction solution confirmed that the target compound of formula 3 was present.

Meanwhile, when the reaction was carried out in the absence of acid catalyst, it was confirmed that a small amount of 3-methanesulfonyl hydroxybutyrolactone was degraded at an early stage of the reaction. Then, methanesulfonic acid was generated therefrom together with furanone without the methanesulfonyl hydroxy group. Methanesulfonic acid, so formed, served as an acid catalyst, and the ring-opening reaction was implemented thereby. However, if the acid catalyst was not separately added, the reaction rate slowed to half of that of the original reaction. Further, the ensuing side reaction such as degradation resulted in lowering the yield of 4-hydroxyl-3-methanesulfonyl hydroxybutyric acid. More specifically, even though an acid catalyst is not separately added at the initial reaction, the ring-opening reaction may occur due to the acid catalyst generated within the reaction. However, it is more preferable to use the acid catalyst in the actual reaction in view of the reaction rate and yield.

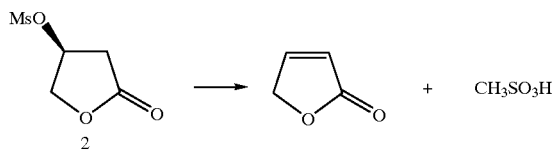

Since the ring-opening reaction is reversible, both the starting material and target ring-opened compound are simultaneously present in the reacting solution. If the solvent is removed for obtaining only the ring-opened compound expressed by formula 3, and the separation of the ring-opened compound is attempted, there is the problem that the ring is closed again to give the result of reverting to the starting material.

With this in mind, the inventors herein have attempted a method of separating and recovering the unreacted starting material through extracting the layer of aqueous solution with an organic solvent. More specifically, the ring-opening reaction of (S)-3-methanesulfonyl hydroxybutyrolactone of formula 2 has been attempted in $D_2O$ solution using sulfuric acid as a catalyst. Then, the reaction solution was extracted with $CH_2Cl_2$ to recover the unreacted starting material. The test results by the nuclear magnetic resonance analyzer showed that 37 mol % of the compound of formula 2 was contained in the $CH_2Cl_2$ solution while 63 mol % of the compound expressed of formula 3 was contained in $D_2O$ solution At the same time, (S)-3-methanesulfonyl hydroxybutyrolactone recovered from the actual reaction was highly pure and could be utilized in the ring-opening reaction without any additional purification process.

The satisfactory results may be produced therefrom since the ring-opened compound expressed by formula 3 is only present in the water layer and not in the organic layer, and vice versa for the unreacted compound expressed by the formula 2. Further, the compound expressed by formula 3, which is present in the water layer, is pure enough to be employed for the next reaction without further purification. It was confirmed that the compound of formula 3 was very stable in the aqueous solution phase, and even after 12 hours of storage at room temperature, recyclization hardly occurred therein.

In addition to the aforementioned dichloromethane, various kinds of solvents, immiscible with water, designed to recover unopened (S)-3-methanesulfonyl hydroxybutyrolactone include the following: haloalkanes such as chloroform, tetrachloromethane, or dichloroethane, aromatic solvents such as benzene, or toluene, and ethyl ether and propyl ether, and so on.

As for the next reaction step, the ring-opened compound of formula 3 undergoes an epoxydation reaction in which its chiral center is inversely converted stereoselectively in the presence of a base. Then, the optically pure salt of 3,4-epoxybutyric acid of formula 4 is prepared therefrom. No such reaction has been disclosed in any of the references, and the resulting salt of 3,4-epoxybutyric acid depends on the base used herein.

The inventors herein have attempted the inverse conversion reaction of 4-hydroxy-3-activated hydroxybutyric acid of formula 3, so obtained via the ring-opening reaction, by epoxidation in the presence of a base. The aqueous solution of 4-hydroxy-3-methanesulfonyl hydroxybutyric acid, so obtained via the ring-opening reaction, was used. Then, the reaction was carried out in the aqueous solution at room temperature using 2.3 equivalent of sodium hydroxide as a base.

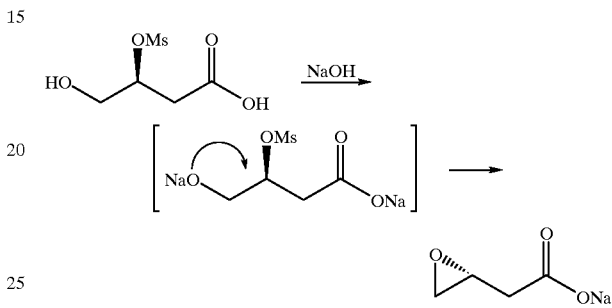

The above reaction showed a remarkable reactivity in view of the fact that the reaction was carried out at room temperature for a short time of less than 30 minutes. When the reacting solution was analyzed by the nuclear magnetic resonance spectrometer, more than 90% conversion rate was duly confirmed. After being acidified, the above solution was extracted with ethyl ether to produce (R)-3,4-epoxybutyric acid with a yield of 55%.

For the epoxydation reaction according to this invention, an inorganic or organic base may be used. More specifically, applicable bases according to this invention include the following:

Alkali metal hydroxide such as potassium hydroxide, sodium hydroxide, and lithium hydroxide, Alkaline earth metal hydroxide such as magnesium hydroxide, calcium hydroxide and barium hydroxide, Alkali metal alkoxide such as sodium methoxide, sodium ethoxide, sodium t-butoxide, Quaternary ammonium hydroxide such as tetrabutyl ammonium hydroxide, benzyltrimethyl ammonium hydroxide, and Alkylamine such as $NR^1R^2R^3$ (wherein, $R^1$, $R^2$ and $R^3$ are alkyl groups of $C_{1\sim7}$, respectively), $NHR^4R^5$ (wherein, $R^4$ and $R^5$ are alkyl group of $C_{2\sim7}$, respectively) and $NH^2R^6$ (wherein, $R^6$ is an alkyl group of $C_{3\sim9}$), i.e., trimethylamine, triethylamine, tripropylamine, dipropylamine, dibutylamine and t-butylamine.

Meanwhile, the amount of a base may be dependent on the strength or kind of alkalinity, but it is preferable to use the base in the equivalent of 1.0 to 4.0.

Based on the above results, the epoxidation of 4-hydroxy-3-methanesulfonyl hydroxybutyric acid methyl ester having an ester group (not carboxyl group) has been attempted using sodium hydride as a base in tetrahydrofuran. However, the inventors herein have failed to produce the target epoxidated compound while only obtaining compounds without the methanesulfonyl group.

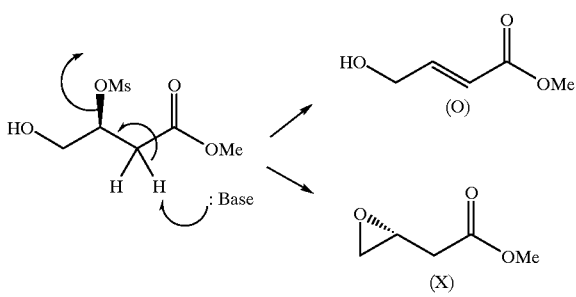

The above results have confirmed that the formation of an anion of the carboxyl group by the treatment of a base is of great importance. In this regard, the hydrogen at the α-position of the carbonyl group may be easily attacked by a base due to its high acidity.

When the carboxyl group of 4-hydroxy-3-methanesulfonyl hydroxybutyric acid is an anion form, the influence of such anion reduces the acidity of the hydrogen at the α-position and consequently makes it difficult for a base to attack. Therefore, the elimination reaction of such methanesulfonyl hydroxy group (—OMs) hardly occurs under said reaction step.

The final reaction step process for the preparing L-carnitine via the reaction between said (R)-3,4-epoxybutyric acid and trimethylamine is similar to some well-known methods [J. Org. Chem., vol. 49, 3707~3711 (1984); Helvetica Chimica Acta, vol. 70, 142~152(1987); European Patent 237,983 (1987)].

The sodium 3,4-epoxybutyrate, so formed from the above reaction, is not separated while the aqueous solution of 25% trimethylamine of 2 equivalent is immediately added to the reacting solution and stirred at 45° C. for 2 hours to yield L-carnitine. The method of separating and purifying L-carnitine from the reacting solution uses a commonly known method, preferably the cation exchange resin (Amberlite IR-120). According to the method of separating and purifying L-carnitine via cation exchange resin (Amberlite IR-120), the optical purity of L-carnitine, so obtained, is more than 95 % with the yield of about 55% or more. Further, similar results may be obtained if the sodium 3,4-epoxybutyrate, so formed during the epoxydation, is neutralized with sulfuric acid and converted into 3,4-epoxybutyric acid, which is reacted with trimethylamine.

Under the process for the preparing L-carnitine according to this invention, (S)-3-activated hydroxybutyrolactone of formula 2 as a raw material is used for consecutively carrying out the ring-opening reaction, inverse conversion reaction of the chiral center by epoxydation, and nucleophilic substitution. Further, low-priced compounds such as sulfuric acid, sodium hydroxide and trimethylamine are used, and continuous reactions are carried out in an aqueous solution in a reactor without separate purification process. Based on such facts, the above process for preparing L-carnitine is expected to be highly useful in the industrial application.

The inverse conversion at the chiral center by epoxydation, one of the pivotal reactions under this invention, is a typical nucleophilic substitution. Based on the characteristics of the chemical reaction, D-carnitine may be prepared from (R)-3-activated hydroxybutyrolactone as a raw material instead of (S)-3-activated hydroxybutyrolactone.

The invention herein is explained in more detail by the following examples but is not limited to these examples.

EXAMPLE 1

Preparation of (S)-3-methane sulfonylhydroxybutyrolactone (S)-3-hydroxy-γ-butyrolactone (10.2 g, 0.10 mol), methanesulfonyl chloride (18.3 g, 0.16 mol) and dichloromethane (100 ml) were placed in a 250 ml reactor. Then, 50% triethylamine-dichloromethane solution (30.4 g, 0.15 mmol) was added dropwise to the mixture at 0° C. for 1 hour. The reacting solution was stirred for 3 hours while maintaining the temperature at 0° C. The solution was extracted with distilled water (100 ml) twice for the removal of the salts therefrom. Dichloromethane solution was dried over magnesium sulfate and filtered. The solvent was slowly concentrated under the reduced pressure to yield the solid thereof. The solid, so formed, was recrystalized with dichloromethane and n-hexane. Then, the crystal was filtered and dried to yield the pure form of (S)-3-methanesulfonyl hydroxybutyrolactone (14.4 g, yield: 80%).

$^1$H-NMR(acetone-d$_6$, ppm): δ2.7~3.2(m, 2H, —CH$_2$CO—), 3.2(s, 3H, CH$_3$SO$_3$—), 4.5~4.8(m, 2H, O—CH$_2$CH(OMs)-), 5.5~5.6(m. 1H, O—CH$_2$CH(OMs)-)

$^{13}$C-NMR(acetone-d$_6$, ppm): δ35.31(—CH$_2$CO—), 37.97 (CH$_3$SO$_3$—), 73.41(—CH$_2$CH(OMs)-), 77.39(O—CH$_2$CH (OMs)-), 174.45(—CH$_2$CO—)

EXAMPLE 2

Preparation of L-carnitine (S)-3-methanesulfonyl hydroxybutyrolactone (10.0 g, 55.6 mmol), water (100 ml), and the concentrated sulfuric acid (0.549 g, 5.60 mmol) were placed in a 250 ml reactor and stirred at 50° C. for 3 hours. The reacting solution was cooled to room temperature and extracted with dichloromethane (100 ml) twice to recover the unreacted (S)-3-methanesulfonylhydroxybutyrolactone (recovery amount: 3.7 g). The target (S)-4-hydroxy-3-methanesulfonyl hydroxybutyric acid was present in an aqueous layer.

An aqueous solution of 3N sodium hydroxide (27.1 ml, 81.3 mmol) was added to the reacting solution containing said (S)-4-hydroxy-3-methanesulfonyl hydroxybutyric acid (35.0 mmol) and stirred at room temperature for 10 minutes. The target sodium (R)-3,4-epoxybutyrate was present in the layer of aqueous solution. An aqueous solution of 25 w % trimethylamine (16.5 g, 69.8 mmol) was added to the reacting solution and stirred at 45° C. for 2 hours. The reacting solution was distilled under the reduced pressure for removing the solvents. The distilled material was dissolved in a small amount of water and placed in a column filled with a cation exchange resin (Amberite IR-120). Then, pure water was fluxed through the column for to remove impurities. When the pH became 7, aqueous solution of 2% ammonia was fluxed to obtain the aqueous solution containing L-carnitine. After removing the solvent under the reduced pressure, the reacting mixture was dissolved in isopropanol at 70° C., and a small amount of undissolved impurities filtered and removed. Thereafter, the resultant material was again concentrated under reduced pressure and recrystallized in the presence of a co-solvent containing isopropanol and acetone to obtain the pure form of L-carnitine(3.1 g, yield: 55%).

$[\alpha]_D^{25}$=−30(c 2, H$_2$O) [Value in reference: $[\alpha]_D^{25}$=−31]

$^1$H-NMR(D$_2$O, ppm): δ2.3(m, 2H, —CH$_2$CO$_2$—H), 3.1 (s, 9H, (CH$_3$)$_3$N$^+$—), 3(m, 2H, (CH$_3$)$_3$N$^+$—CH$_2$—), 4.4 (m, 1H, —CH(OH—)

$^{13}$C-NMR(D$_2$O, ppm): δ43.35(—CH$_2$CO$_2$—H), 54.41(t, J=4Hz, (CH$_3$)$_3$N$^+$—), 41(—CH(OH)-), 70.44((CH$_3$)$_3$N$^+$—CH$_2$—), 178.25(—CH$_2$CO$_2$—H)

EXAMPLE 3

Preparation of (S)-4-hydroxy-3-methanesulfonyl hydroxybutyric acid (S)-3-methanesulfonyl hydroxybutyrolactone (1.0 g, 5.6 mmol), $D_2O$ (10 ml), and the concentrated sulfuric acid (0.0549 g, 0.56 mmol) were placed in a 25 ml reactor and stirred at 50° C. for 3 hours. The reacting solution was cooled to room temperature and extracted with dichloromethane (10 ml) twice to recover the unreacted (S)-3-methanesulfonyl hydroxybutyrolactone. The presence of the target (S)-4-hydroxy-3-methanesulfonyl hydroxybutyric acid in a pure form in the $D_2O$ layer was confirmed by nuclear magnetic resonance.

$^1$H-NMR($D_2O$, ppm): δ2.6~2.8(m, 2H, —$CH_2CO_2H$), 3.1(s, $OSO_2CH_3$), 3.6~3.9(m,2H, $HOCH_2$—), 4.9~5.1(m, 1H, —CH(OMs)-)

$^{13}$C-NMR($D_2O$, ppm): δ36.27(—$CH_2CO_2H$), 38.15 ($OSO_2CH_3$), 62.94(—CH(OMs)-), 80.81($HOCH_2$—), 174.04(—$CH_2CO_2H$)

EXAMPLE 4

Preparation of sodium (R)-3,4-epoxybutyrate

The aqueous solution of 3N sodium hydroxide (2.7 ml, 8.1 mmol) was added to the reaction solution containing (S)-4-hydroxy-3-methanesulfonyl hydroxybutyric acid, so prepared from Example 3 and stirred at room temperature for 10 minutes. The presence of the target sodium (R)-3,4-epoxybutyrate in a pure form in the layer of the reacting solution was confirmed by nuclear magnetic resonance.

$^1$H-NMR($D_2O$, ppm): δ2.3~2.5(m, 2H, $CH_2$—$CO_2Na$), 2.6~2.9(m, 2H), 3.2~3.3(m, 1H) $^{13}$C-NMR($D_2O$, ppm): δ40.87(—$CH_2$—$CO_2Na$), 48.24(4-$CH_2$), 51.08(3-CH), 179.41(—$CO_2Na$)

EXAMPLE 5

Preparation of sodium (R)-3,4-epoxybutyrate

Sodium methoxide (438 mg, 8.11 mmol) was added to the reacting solution of $D_2O$ containing (S)-4-hydroxy-3-methanesulfonyl hydroxybutyric acid, so prepared from Example 3 and stirred at room temperature for 20 minutes. The presence of the target sodium (R)-3,4-epoxybutyrate in the layer of the reacting solution was confirmed by nuclear magnetic resonance.

$^1$H-NMR($D_2O$, ppm): δ2.3~2.5(m, 2H, $CH_2$—$CO_2Na$), 2.6~2.9(m, 2H), 3.2~3.3(m, 1H, 3-H)

$^{13}$C-NMR($D_2O$, ppm): δ40.89(—$CH_2$—$CO_2Na$), 48.25 (4-$CH_2$), 51.10(3-CH), 179.37(—$CO_2Na$)

EXAMPLE 6

Preparation of calcium (R)-3,4-epoxybutyrate

Calcium hydroxide (340 mg, 4.59 mmol) was added to the reacting solution of $D_2O$ containing (S)-4-hydroxy-3-methanesulfonyl hydroxybutyric acid, so prepared from the Example 3 and stirred at room temperature for 30 minutes. The presence of the target calcium (R)-3,4-epoxybutyrate in the layer of the reacting solution was confirmed by nuclear magnetic resonance.

$^1$H-NMR($D_2O$, ppm): δ2.3~2.4(m, 2H, $CH_2$—$CO_2Ca$), 2.5~2.8(m, 2H, 3.2~3.3(m, 1H, 3-H)

$^{13}$C-NMR($D_2O$, ppm): δ40.78(—$CH_2CO_2Ca$), 48.23(4-$CH_2$), 51.05(3-CH), 179.52(—$CO_2Ca$)

EXAMPLE 7

Preparation of tetrabutyl ammonium (R)-3,4-epoxybutyrate 1.0 M methanol solution of tetrabutyl ammonium hydroxide (8.12 ml, 8.12 mmol) was added to the reacting solution of $D_2O$ containing (S)-4-hydroxy-3-methanesulfonyl hydroxybutyric acid, so prepared from Example 3 and stirred at room temperature for 30 minutes. The presence of the target tetrabutyl ammonium (R)-3,4-epoxybutyrate in the layer of the reacting solution was confirmed by nuclear magnetic resonance.

$^1$H-NMR($D_2O$, ppm): δ2.2~2.3(m, 2H, $CH_2$—$CO_2NBu_4$), 2.5~2.8(m, 2H), 3.2~3.3(m, 1H, 3-H)

$^{13}$C-NMR($D_2O$, ppm): δ41.09(—$CH_2$—$CO_2NBu_4$), 48.23(4-$CH_2$), 51.14(3-CH), 178.54(—$CO_2NBu_4$)

EXAMPLE 8

Preparation of triethyl ammonium (R)-3,4-epoxybutyrate

Triethylamine (790 mg, 7.81 mmol) was added to the reacting solution of $D_2O$ containing (S)-4-hydroxy-3-methanesulfonyl hydroxybutyric acid, so prepared from Example 3 and stirred at room temperature for 30 minutes. The presence of the target triethyl ammonium (R)-3,4-epoxybutyrate in the layer of the reacting solution was confirmed by nuclear magnetic resonance.

$^1$H-NMR($D_2O$, ppm): δ2.2~2.4(m, 2H, $CH_2$—$CO_2HNEt_3$), 2.5~2.8(m, 2H), 3.1~3.2(m, 1H, 3-H)

$^{13}$C-NMR($D_2O$, ppm): δ40.94(—$CH_2$—$CO_2HNEt_3$), 48.15(4-$CH_2$), 51.04(3-CH), 178.97(—$CO_2HNEt_3$)

EXAMPLE 9

Preparation of diisopropyl ammonium (R)-3,4-epoxybutyrate

Diisopropyl amine (790 mg, 7.81 mmol) was added to the reacting solution of $D_2O$ containing (S)-4-hydroxy-3-methanesulfonyl hydroxybutyric acid, so prepared from Example 3 and stirred at room temperature for 2 hours. The presence of the target diisopropyl ammonium (R)-3,4-epoxybutyrate in the layer of the reacting solution was confirmed by nuclear magnetic resonance.

$^1$H-NMR($D_2O$, ppm): δ2.2~2.4(m, 2H, $CH_2$—$CO_2HN(H)Pr^i_2$), 2.5~2.8(m, 2H), 3.1~3.2(m, 1H, 3-H)

$^{13}$C-NMR($D_2O$, ppm): δ40.92(—$CH_2$—$CO_2HN(H)Pr^i_2$), 48.12(4-$CH_2$), 51.02(3-CH), 178.95(—$CO_2HN(H)Pr^i_2$)

EXAMPLE 10

Preparation of t-butyl ammonium (R)-3,4-epoxybutyrate t-butyl amine (571 mg, 7.81 mmol) was added to the reacting solution of $D_2O$ containing (S)-4-hydroxy-3-methanesulfonyl hydroxybutyric acid, so prepared from Example 3 and stirred at room temperature for 4 hours. The presence of the target t-butyl ammonium (R)-3,4-epoxybutyrate in a layer of the reacting solution was confirmed by nuclear magnetic resonance.

$^1$H-NMR($D_2O$, ppm): δ2.1~2.4(m, 2H, $CH_2$—$CO_2HNH_2Bu^t$), 2.5~2.8(m, 2H), 3.1~3.2(m, 1H, 3-H)

$^{13}$C-NMR($D_2O$, ppm): δ40.88(—$CH_2$—$CO_2HNH_2Bu^t$), 48.13(4-$CH_2$), 51.01(3-CH), 179.10(—$CO_2HNH_2Bu^t$)

The process for preparing L-carnitine according to this invention may be very useful in an industrial scale in that a) less organic solvent is used and low-priced compounds are utilized in aqueous solution, and b) the high yield and purity of the final product make it possible to continuously carry out the reaction in a reactor without separate purification processes.

What is claimed is:

1. A process for preparing L-carnitine of the following formula (1) from (S)-3-activated hydroxybutyrolactone, wherein
   (S)-3-activated hydroxybutyrolactone of the following formula (2) is subjected to a ring-opening reaction in an aqueous solvent;
   4-hydroxy-3-activated hydroxybutyric acid of the following formula (3) is prepared therefrom;
   4-hydroxy-3-activated hydroxybutyric acid of said formula (3) is subjected to an inverse conversion reaction at the chiral center in the presence of a base in order to prepare the salt of 3,4-epoxybutyric acid of the following formula (4); and
   the salt of 3,4-epoxybutyric acid of said formula (4) undergoes a nucleophilic substitution by trimethylamine,

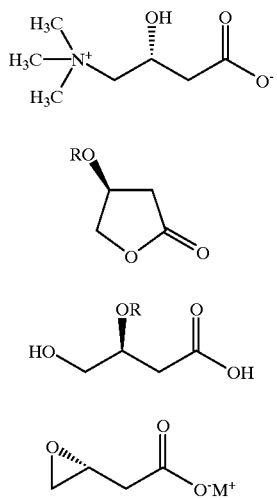

wherein R is chosen from alkylsulfonyl groups, arylsulfonyl groups, acyl groups, and phosphoryl groups, and M is determined by the salt used herein.

2. A process for preparing L-carnitine according to claim 1, wherein said R is chosen from alkylsulfonyl groups and haloalkylsulfonyl groups, wherein the alkyl contains from $C_1$ to $C_{12}$; benzenesulfonyl groups; naphthalene sulfonyl groups; alkoxy benzenesulfonyl groups; and nitrobenzenesulfonyl groups.

3. A process for preparing L-carnitine according to claim 2, wherein said R is a methanesulfonyl group.

4. A process for preparing L-carnitine according to claim 1, wherein said ring-opening reaction is carried out in the presence of water as a single solvent or co-solvent containing water and organic solvent.

5. A process for preparing L-carnitine according to claim 4, wherein said organic solvent is chosen from alcohols of $C_1$ to $C_4$, tetrahydrofuran, and acetonitrile.

6. A process for preparing L-carnitine according to claim 1 or 4, wherein said ring-opening reaction is carried out in the presence of acid catalyst.

7. A process for preparing L-carnitine according to claim 6, wherein said acid catalyst is chosen from sulfuric acid, hydrochloric acid, phosphoric acid, methanesulfonic acid, toluenesulfonic acid, and camphorsulfonic acid.

8. A process for preparing L-carnitine according to claim 1, wherein said inverse conversion reaction is carried out in the presence of a base, which is chosen from alkali metal hydroxides, alkaline earth metal hydroxides, alkali metal alkoxides, and quaternary ammonium hydroxides.

9. A process for preparing L-carnitine according to claim 8, wherein said alkali metal hydroxides are chosen from sodium hydroxide, potassium hydroxide, and lithium hydroxide.

10. A process for preparing L-carnitine according to claim 8, wherein said alkaline earth metal hydroxides are chosen from magnesium hydroxide, calcium hydroxide, and barium hydroxide.

11. A process for preparing L-carnitine according to claim 8, wherein said alkali metal alkoxides are chosen from sodium methoxide, sodium ethoxide, and sodium t-butoxide.

12. A process for preparing L-carnitine according to claim 8, wherein said quaternary ammonium hydroxides are chosen from tetrabutyl ammonium hydroxide and benzyltrimethyl ammonium hydroxide.

13. A process for preparing L-carnitine according to claim 1, wherein said inverse conversion reaction is carried out in the presence of an alkylamine base.

14. A process for preparing L-carnitine according to claim 13, wherein said alkylamine base is chosen from $NR^1R^2R^3$, wherein $R^1$, $R^2$, and $R^3$ are independently chosen from alkyl groups comprising from $C_1$ to $C_7$.

15. A process for preparing L-carnitine according to claim 13, wherein said alkylamine is chosen from $NHR^4R^5$, wherein $R^4$ and $R^5$ are independently chosen from alkyl groups comprising from $C_2$ to $C_7$.

16. A process for preparing L-carnitine according to claim 13, wherein said alkylamine is chosen from $NH_2R^6$, wherein $R^6$ is chosen from alkyl groups comprising $C_3$ to $C_9$.

17. A process for preparing L-carnitine according to claim 8 or 13, wherein said base is employed in the equivalent ratio of from 1.0 to 4.0 with respect to said formula 3.

18. A process for preparing L-carnitine according to claim 1, wherein the process comprises at least three discrete reaction steps.

19. A process for preparing L-carnitine according to claim 1, wherein the process is carried out continuously in a reactor without separate purification processes.

* * * * *